Figure 1:
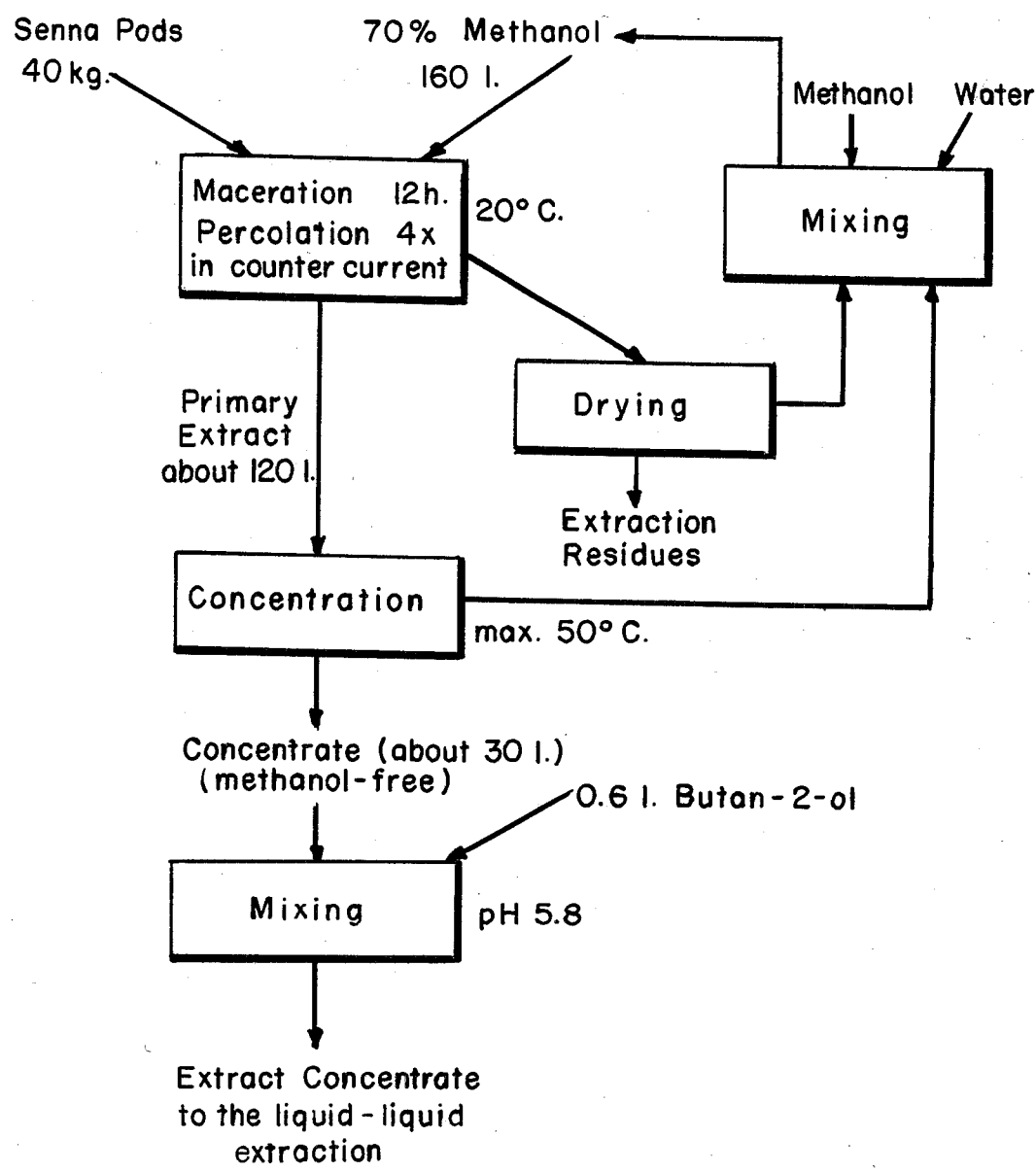

United States Patent [19]

Hietala

[11] Patent Number: 4,595,592
[45] Date of Patent: Jun. 17, 1986

[54] PROCESS FOR OBTAINING LAXATIVE COMPOUNDS FROM SENNA DRUGS

[75] Inventor: Pentti Hietala, Helsinki, Finland

[73] Assignee: Dr. Madaus & Co., Cologne, Fed. Rep. of Germany

[21] Appl. No.: 676,203

[22] Filed: Nov. 28, 1984

Related U.S. Application Data

[63] Continuation of Ser. No. 591,900, Mar. 21, 1984, abandoned, which is a continuation of Ser. No. 337,059, Jan. 5, 1982, abandoned.

[51] Int. Cl.$^4$ ............................................ A61K 35/78
[52] U.S. Cl. .................................................. 424/195.1
[58] Field of Search ...................................... 424/195.1

[56] References Cited

FOREIGN PATENT DOCUMENTS 1617667  9/1970  Fed. Rep. of Germany .

OTHER PUBLICATIONS

Synthelabo 2915063 Apr. 12, 1979.

Remington's Practice of Pharmacy 9th ed., The Mack Pub. Co., Easton, Pa., Crystallization, p. 208, 1948.

*Primary Examiner*—Albert T. Meyers
*Assistant Examiner*—John W. Rollins
*Attorney, Agent, or Firm*—Felfe & Lynch

[57] ABSTRACT

The present invention provides a process for obtaining laxative compounds from senna drug, wherein
(a) the senna drug is extracted with aqueous methanol by countercurrent percolation and the extract concentrated at a temperature of $\leq 50°$ C. until the methanol has been completely removed from the extract;
(b) the extract obtained is purified by continuous liquid-liquid extraction with an organic solvent;
(c) the refined material (raffinate) obtained is transferred to a crystallization apparatus, acidified, while stirring, to a pH of 1.5 to 2.0, seeded with sennoside crystals, left to crystallize while stirring and the crystalline crude sennoside obtained separated off;
(d) whereafter, the crude sennoside are, if desired, recrystallized and optionally converted with a pharmacologically compatible base into a pharmacologically compatible salt.

13 Claims, 3 Drawing Figures

FIG. I.
EXTRACTION

LIQUID-LIQUID EXTRACTION

RECRYSTALLIZATION

PROCESS FOR OBTAINING LAXATIVE COMPOUNDS FROM SENNA DRUGS

This application is a continuation of application Ser. No. 591,900, filed Mar. 21, 1984, now abandoned, which is a continuation of application Ser. No. 337,059, filed Jan. 5, 1982, now abandoned.

The present invention is concerned with a process for obtaining laxative compounds from senna drug.

Senna drug consists of the dried leaves and pods of the senna plant, for example, of Indian senna (*Cassia angustifolia*) and of Egyptian senna (*Cassia acutifolia*). The laxative action of the senna drug is due to a chemical compound, namely, the sennoside.

The laxative-active substances in the senna drug are bimolecular glycoside derivatives of the two anthracene compounds rhein and aloe-emodin. The most important are sennosides A, B, $A_1$, C and D. Sennosides A, B and $A_1$ are bis-glucosylrhein anthrones and sennosides C and D are glycosylrhein-glycosyaloe-emodin dianthrone compounds.

In addition to the sennosides, the crude drug also contains aglucones (sennidines) and other decomposition products and derivatives of the sennosides. Some of these can also have a laxative effect but, at the same time, can also be toxic and give rise to undesirable side effects. Side effects which are typical for senna preparations include nausea, vomiting, wind, colic and diarrhea.

Various processes have been described for extracting the laxative-active substances from the senna drug. The most important laxative-active glucosides, i.e., sennosides A and B, were isolated from the senna drug for the first time by Stoll et al. (see Helv. Chim. Acta, XXXII, Fasciculus VI (1949), 1892). Subsequently, many patents [specifications] have been published which describe processes for the preparation of sennoside concentrates.

Hitherto, the preparation of the senna extract has generally been carried out in two stages. In the first stage, vegetable pigments, fats, and other impurities are removed with an approprite solvent, for example chloroform, ether (U.S. Pat. No. 3,089,814) or with 90% methanol (Federal Republic of Germany Published examined Application No. 16 17 667). After this preliminary extraction, the active glucosides are extracted from the drug in the second stage with methanol, aqueous methanol, aqueous ethanol or only with water.

In order to facilitate the extraction, the methanol used can be rendered alkaline by the addition of organic bases (Federal Republic of Germany Pat. No. 23 397). The organic bases form methanol-soluble salts with the sennosides which can easily be extracted. However, a disadvantage of this process is that the extract contains a higher content of impurities.

It has also been suggested to use extraction solvents acidified with citric acid (French Pat. No. M 6611 (1969)) or with oxalic acid (British Pat. No. 832,017). In the latter case, 70% ethanol was used as solvent. If acidic methanol or acidic aqueous methanol is used for the extraction, the content of impurities in the extract is smaller than when the extraction is carried out with basic solvents or with water alone. However, these processes have the disadvantage that the sennosides, which are acidic compounds, are, as free acids, only sparingly soluble in the solvents used. Consequently, the amount of solvent required for the extraction is very large and can be as much as 15 to 30 times of the weight of the drug used.

For the extraction of the drug, it is also known to use mixtures of methanol-tetrahydrofuran, methanol-dioxan and tetrahydrofuran-dioxan acidified with phosphoric acid (Hung, Teljes, 6006 (1973)) and aqueous phosphoric acid (Federal Republic of Germany Published examined Application No. 16 17 667) as solvents. However, aqueous solvents activate the glucosidase enzyme so that part of the active glucosides are hydrolyzed, especially when using weakly acidic solutions, the pH value of which corresponds to that of the original plant material. This results in a reduction of the amount of active material in the extract (also Federal Republic of Germany Published Application No. 29 15 063).

In the prior art processes, the sennoside concentrates are obtained from the extracts in various ways.

A solid, sonnoside-containing extract is obtained by gentle drying of the extract (Federal Republic of Germany Published Examined Application No. 16 17 667). The product then contains all the substances present in the extract, the sennoside content of the product being about 17 to 18%.

However, the sennosides can be separated more selectively when they are precipitated from aqueous solutions by the addition of organic solvents. The product obtained contains less ballast materials and has a sennoside content of up to 60 to 70%. The precipitation can be carried out by the addition of diethyl ether (French Patent No. M 6611 Magyar G. et al., Hung. Teljes, 6006 (1973)), isopropyl alcohol, after treatment with a strongly acid ion exchange resin (British Pat. No. 832,017) or ethanol (see Finnish Pat. No. 41588). The sennosides in solution can possibly be converted into the calcium salts (see U.S. Pat. No. 3,089,814 and Finnish Pat. No. 41588) and subsequently precipitated out by the addition of organic solvents so that the active glucosides are obtained as calcium salts. The content of sennosides in the precipitated product then amounts to about 60 to 70%.

For obtaining pure sennosides as free acids, the sennosides are isolated as calcium salts and these salts then decomposed with oxalic acid (see Stoll et al., Helv. Chim. Acta, XXXII, Fasciculus VI (1949), 1892).

Thus, according to these known processes, extracts and various kinds of concentrates containing laxative-active substances can be produced from the senna drug. The amount of laxative-active substances in the concentrates depends upon the content of these substances in the original drug and upon the production process used. The difficulty in the standardization of the senna preparations is the determination of the senna glycosides. The drug contains various compounds which are included in the determination of the senna glycosides. However, the physiological action of these individual compounds is not the same. Since, with the help of conventional methods of determination, it is not possible to differentiate the senna glycosides from the other compounds which have different physiological actions and possibly side reactions, it is difficult to produce preparations, starting from conventional senna extracts, which always produce the same and reproducible action with the same dose.

It is an object of the present invention to provide a process for obtaining laxative compounds from the senna drug which permits the laxative-active substances to be obtained in improved yield in the most concentrated form possible, which are as free as possible with components with undesired side effects.

Thus, according to the present invention, there is provided a process for obtaining laxative compounds from senna drug, wherein.

(a) the senna drug is extracted with aqueous methanol by countercurrent percolation and the extract concentrated at a temperature of $\leq 50°$ C. until the methanol has been completely removed from the extract;

(b) the extract obtained is purified by continuous liquid-liquid extraction with an organic solvent;

(c) the refined material (raffinate) obtained is transferred to a crystallization apparatus, acidified, while stirring, to a pH of about 1.5 to 2.0, seeded with sennoside crystals, left to crystallize while stirring and the crystalline crude sennoside obtained separated off;

(d) whereafter the crude sennosides are, if desired, recrystallized.

The crude sennoside may be recrystallized and may optionally be converted with a pharmacologically compatible base into a pharmacologically compatible salt.

For carrying out the process according to the present invention, mixtures of methanol and water are used in which the sennosides are soluble. It is preferable to use 70% methanol since the maximum solubility of the sennosides lies at a methanol concentration of 60 to 70%. The extraction is carried out in portions and preferably at a slightly elevated temperature but at most at a solvent temperature of $+35°$ C. Since there is a danger that the sennosides would decompose, elevated temperatures have previously been avoided. However, it has surprisingly been found that the sennosides do not decompose at a slightly elevated temperature when methanol is used as solvent.

The drug extraction is carried out in a countercurrent percolation plant. In general, 2 to 4 percolators are used. If the extraction solvent is to be warmed, it is allowed to circulate through an external heat exhanger in which it is thereby warmed to the desired temperature but at most to 35° C. The more percolators are used, the less must the solvent be warmed. The extract obtained then contains less harmful impurities and the sennosides crystallize outmore completely from the mother liquor.

Before the extraction, it is preferable to swell the dry drug in a solvent, for which purpose it is preferable to use the post-percolate from a previously extracted drug. For this purpose, the dry drug is placed in a purcolator, covered with a perforated plate with a weight of about 0.7 kg./dm$^2$ and the solvent or post-percolate passed in. The weight of the amount of solvent required is about three times the weight of the dry drug. It is preferably left to stand overnight and the extraction is commenced the next day.

The extraction takes place over the course of 16 to 20 hours, during which time the necessary amount of 70% methanol is allowed to flow through the dry mass. Since it is preferable to use several percolators, when carrying out the extraction the solvent is first passed into the percolator of the series of percolators which contains the weakest drug, i.e., the one which has already been most extracted and which is to be the next one to be emptied. The solvent is passed from this percolator to the next percolator and so forth. The main extract is taken from the percolator which was the last one to be filled. After removal of an appropriate amount of extract, there is additionally obtained a post-percolate which can be used for swelling a new batch of dry drug. For this purpose, the percolator containing the weakest drug is emptied, filled with portion of the drug, the post-percolate passed in and the extraction carried out on the next day.

According to the process of the present invention, it is possible to extract 1 part of the dry drug with only 4 parts of extraction solvent. If 70% methanol is used at room temperature, then the residual amount of substance in the drug is about 41% per percolator in the series of percolators. With two percolators, the extraction yield is $(1-0.41^2)\times 100 = 83\%$ and with three percolators connected in series it is $(1-0.41^3)\times 100 = 93\%$.

After the extraction, the methanol is removed practically quantitatively from the percolate, the volume of the bottom product obtained being about one fifth of the volume of the percolate. The methanol is removed with the use of a vacuum distillation apparatus equipped with a fractionation column. Because of the danger of hydrolysis of the sennosides, the temperature most not exceed $+50°$ C.

After distilling off the methanol, the concentrate is purified by liquid-liquid extraction with an organic solvent. The solvent used can be an alcohol or ketone which is partly soluble in water, for example, butanol, methyl ethyl ketone or methyl isopropyl ketone, the preferred solvent being butan-2-ol. The liquid-liquid extraction is carried out as a continuous process in a partitioning apparatus with a separation effect of about 10 theoretical steps. The pH of the fed-in concentrate solution is about 5.4 to 5.6 since, at this pH, the salts of the aglucone compounds present in the senna drug are hydrolyzed to such an extent that the aglucones are removed practically quantitatively from the raffinate.

Before use, the butan-2-ol employed for the extraction is preferably saturated with water. The fed-in concentrate which is to be extracted is very concentrated solution with a content of dry material of about 20 to 30%. It contains salts, sugars, amino acids and other water-soluble compounds which originate from the plant mass. The extraction is preferably carried out in such a manner that the run-off ratio of butan-2-ol:raffinate is about 0.7 to 0.8:1.

By means of the liquid-liquid extraction, fats, harmful plant pigments, chlorophylls and carotinoids, free fatty acids, steroids, agluconic anthracene derivatives, neutral glucosides, vegetable waxes and wax alcohols, flavones and other phenols, etc., are removed from the solution. In this way, the raffinate obtained is free from harmful impurities to such an extent that the main amount of the sennosides can be crystallized out directly from the raffinate phase by acidification with a mineral acid to a pH of about 1.2 to 2.0, the mineral acid used preferably being hydrochloric or sulfuric acid.

In order to crystallize the sennosides from the raffinate phase, the sennosides are placed in a container and an amount of acid is passed in, while stirring, until the pH value of the solution is about 1.5 to 2.0. The solution is then seeded with sennoside crystals and left to crystallize for 1 week, while stirring.

Alternatively, the crystallization can also be carried out in a continuously operating crystallization apparatus. The raffinate phase thereby remains for about 1 week in this crystallization apparatus and is divided between 2 or more containers connected in series which discharge into a decanter. The crystallization containers are continuously gently stirred and, for acidification, a solution of the mineral acid is introduced, with stirring, into the first container. The vertical laminar flow in the decanter is about 0.3 to 0.4 mm./minute. This rate of flow ensures a satisfactory sedimentation. The crystallized product is filtered off, washed with water and methanol or acetone and then dried. If desired, the crude product is recrystallized, as is explained hereinafter.

The crude sennosides obtained after the crystallization can, if desired, be recrystallized. For this purpose, the crude sennosides are suspended in a mixture of acetone and water (50:50) to give an approximately 10% suspension, dissolved by the addition of sodium hydroxide to a pH of about 7.5 to 9, with sodium salt formation, and the sennosides again precipitated out by adjusting the solution with hydrochloric acid of a pH of about 1.5 to 2, separated off, washed with aqueous acetone and dried.

Thus, with the process according to the present invention, it is possible to obtain the sennosides in almost 100% purity from the crude drug. In addition, in the case of the process according to the present invention for obtaining laxative-active substances from senna drug, a preliminary extraction of the drug is no longer required, as is necessary in the case of the previously known processes.

Since the sennosides obtained by the process according to the present invention are chemically and pharmacologically completely characterized, they can be used for the formulation of medicinal compositions with definite galenical properties. In contradistinction thereto, according to the previously known processes, only more or less indefinite galenical extracts can be obtained.

The following Examples are given for the purpose of illustrating the present invention:

EXAMPLE 1

40 kg. amounts of senna drug each are placed into two series-connected percolators with a volum of 250 liters which are covered with perforated steel plates. The solvent used for the extraction is 70% methanol which is supplied to the drug in the first percolator. A bottom plate covered with a filter cloth is present on the bottom of the percolator. By means of an emptying cock provided below this plate, the solution is passed to the drug present in the second percolator, whereby the solvent is being allowed to flow freely through the first percolator. By means of a siprom lever, pipetle German "Heber" the solvent is carried from the emptying cock of the first percolator to the second percolator. The rate of flow of the solvent is adjusted by means of the emptying cock on the first percolator. The run-off on the second percolator is adjusted in such a manner that the level of the solvent in the second percolator is high enough to cover the perforated steel plate, which has a weight of 0.7 kg./dm$^2$.

For the extraction of 40 kg. of senna drug, a total of 160 liters of solvent are used. After this amount of 70% methanol has passed through both percolators and an appropriate amount of percolate has been collected, the emptying pipe of the percolator is connected to a post-percolate container and an additional 60 liters of 70% methanol are passed through the percolators. Thereafter, residual free solvent is passed from the first percolator into the upper part of the second percolator and the post-percolate is collected until a total of 120 liters have been obtained. The first percolator is then emptied, again filled with 40 kg. senna drug and the post-percolate is pumped onto the drug, 120 liters of post-percolate being sufficient to cover the drug in the percolator. Subsequently, a piped connection is made from the run-off to a pump and a heat exchanger and from there to the cover of the percolator and the solution is allowed to circulate until the temperature of the solution is +30° C. It is then left to stand overnight.

The following day, this percolator is connected to the one previously extracted and the extraction carried out in the above-described manner.

For each 40 kg. of drug 160 liters of percolate are collected from which the methanol is removed in a vacuum rotary evaporator equipped with a packed column. About 30 liters of bottom product are obtained which is extracted in the "mixer-settler" apparatus (10 stage) using 40 liters of water-saturated butan-2-ol. About 38 to 40 liters of aqueous raffinate are obtained and about 30 to 32 liters of butan-2-ol extract. The aqueous raffinate is acidified with 93% sulfuric acid, while stirring, for 20 hours, 1.6% by volume (calculated on the volume of liquid to be acidified) thereby being used. The acidified solution then has a pH of 1.5 to 2.0. After stirring for a further 6 days, the precipitate is allowed to deposit overnight, filtered, washed with water until the wash water is colourless, washed with methanol and dried in a current of air at room temperature. The yield per 40 kg. of raw material is 760 to 790 g. (dry substance) with a sennoside content of 90 to 94%. Thus, the yield is about 70% of the amount of sennoside present in the raw material.

0.5 kg. of crude product is suspended in 5 liters of an acetone-water mixture (1:1 v/v), 48% aqueous sodium hydroxide are added thereto, while stirring, until the pH of the solution is 8.5 to 9. Insoluble residue is filtered off and 35% hydrochloric acid is added to the filtrate until the pH of the solution is 1.5 to 2. Stirring is continued until crystallization commences and then the solution is left to crystallize for at least 3 hours. The precipitate is filtered off from the solution, washed on the fliter with 0.5 liter of water and 0.5 liter of acetone and dried at room temperature with a current of air. Four fifths of the mother liquor can be mixed with wash water and wash acetone and this solution used as crystallization solvent for the next equally large portion of crude product. The yield per 0.5 kg. of crude product is 0.460 kg. (dry substance) with a sennoside content of 98 to 99%.

EXAMPLE 2

The procedure described in Example 1 is employed but using three series-connected percolators and without warming the 70% methanol. Otherwise the procedure is as described in Example 1, using 160 liters of solvent per 40 kg. of drug. From 40 kg. of drug there is obtained 0.890 kg. of sennoside crude product with a sennoside content of 92% (dry substance). The crude product can be recystallized as in Example 1.

EXAMPLE 3

Extraction, removal of methanol from the extract and liquid-liquid extraction are carried out as described in Example 1. After the treatment with butan-2-ol, the sennoside mixture is crystallized from the raffinate in a continuously-operating crystallization apparatus. For the crystallization, use is made of two containers, connected one after the other, and a third container as decanter, which is connected in series to the others. Sedimentation of the sennoside mixture is carried out in the latter container, the main amount of the precipitate thereby being separated from the mother liquor. For this purpose, the raffinate phase obtained after the purification with butan-2-ol is passed at a rate of about 2 liters/hour into the first container. 93% Sulfuric acid is simultaneously pumped, in an amount of 1.6% by volume of the raffinate, into this container. In order to prevent sedimentation at this point, the liquid in the first container is stirred continuously. The suspension from the first container is then passed via an unrestricted overflow into the second container, which is also equipped with a stirrer, and from there, via an unrestricted overflow, into the third container, where the precipitate is allowed to settle, the mother liquor being allowed to run off via an unrestricted overflow to a waste solvent container. The precipitate is removed from the third decanter, through a cock provided on the bottom thereof, in the form of a thick suspension which is filtered with a suction filter, washed with water and methanol and dried in a current of air at ambient temperature. The yield per 40 kg. of crude material used is 790 g., the sennoside content of which is 91%.

EXAMPLE 4

Figure 2:
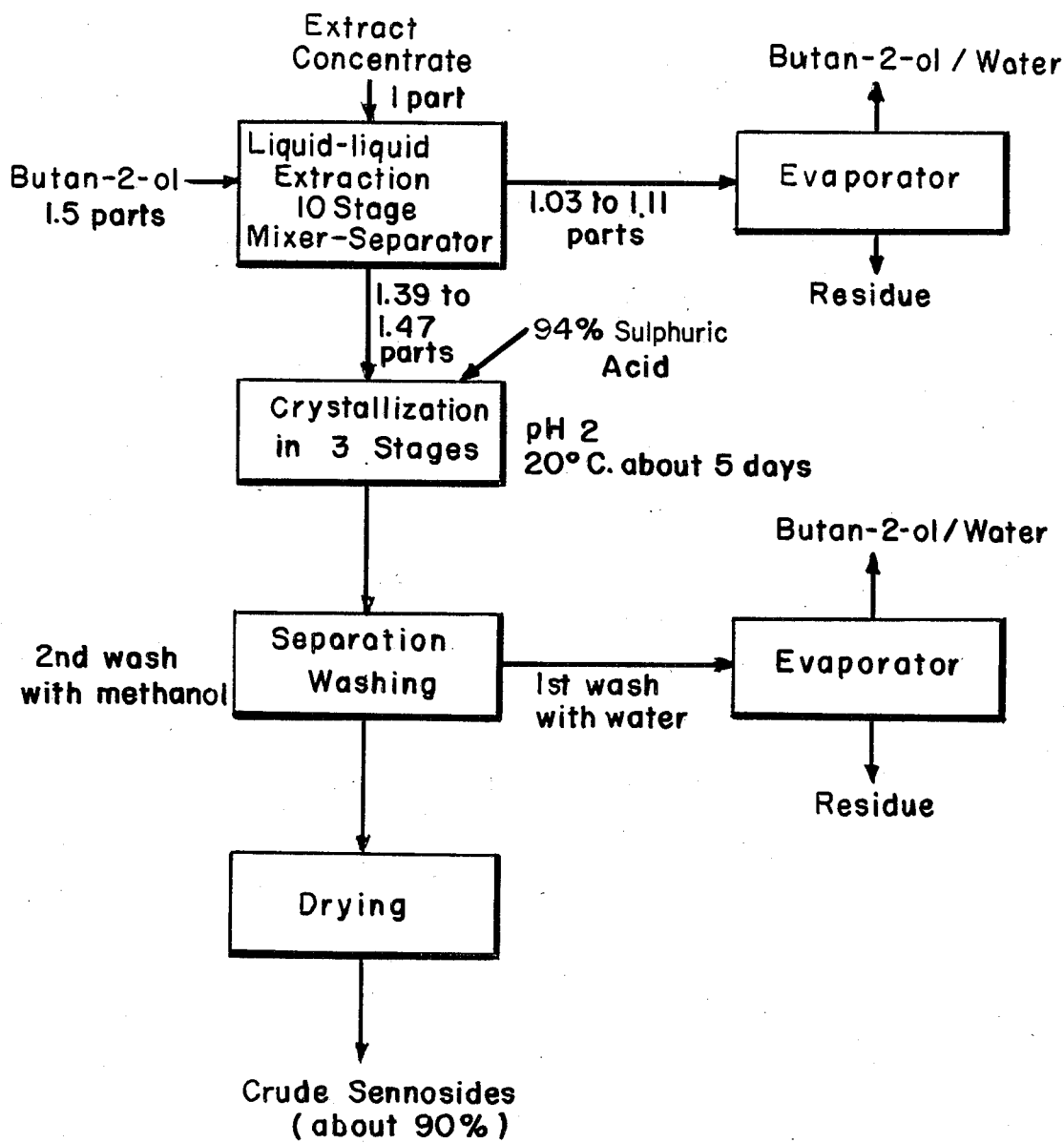
Figure 3:
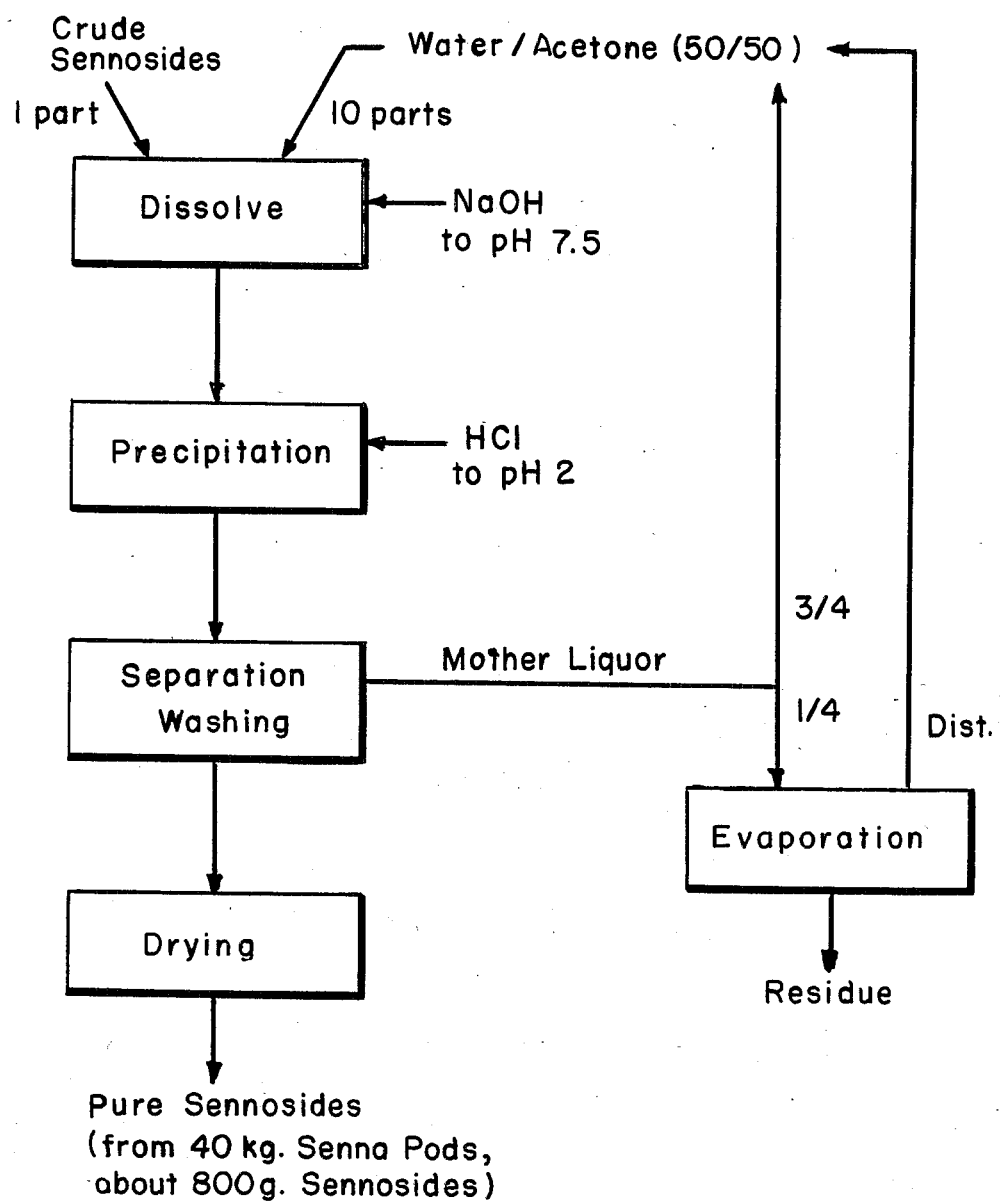

The extraction, liquid-liquid extraction and recrystallization described in the following are illustrated schematically in FIGS. 1, 2 and 3 of the accompanying drawings.

The drug is extracted at room temperature in a 4-stage countercurrent percolation plant. For this purpose, 40 kg. of senna pods are introduced daily into one of four conical containers and weighed down with a perforated plate.

70% Methanol is passed in countercurrent through the battery of 4 percolators in an amount such that the freshly introduced pods are completely covered with liquid. After a maceration period of at least 12 hours, percolation is continued until a total of about 160 liters of 70% methanol have passed through. From the container covered with fresh solvent, the extraction liquid is then passed completely into the next container connected in series and the extraction residue dried in order to recover the solvent. The container is now ready to receive the next 40 kg. batch of drug and this is switched over to the end of the battery. The degree of efficiency of the extraction per percolation stage is about 60%. From each 40 kg. of senna pods, there are obtained about 120 liters of primary extract which are concentrated to about 30 liters under vacuum in a rotary evaporator equipped with a fractionating column. The temperature in the product container must thereby not exceed 50° C.

In order to keep the following liquid-liquid extraction free from disturbance, the methanol must be completely removed. After ascertaining gas chromatographically that the concentrate is free from methanol, it is subsequently mixed with about 2% of butan-2-ol. The pH value of this extract is about 5.8.

For the subsequent liquid-liquid extraction the concontrate is passed in a 10-stage mixer settler battery (each stage about 5 liters), without previous filtration, counter to butan-2-ol. At a run-in ratio of butan-2-ol:extract concentrate of 1.5:1, the ratio of butan-2-ol extract:extract raffinate is 0.7 to 0.8:1. The average residence time for each stage is about 20 minutes.

The extract raffinate is then adjusted with 94% sulfuric acid to a pH of 2 and passed to a 3-stage crystallization apparatus.

To initiate the crystallization, it is seeded and then left to crystallize at room temperature for 5 days. The crystal slurry obtained is removed from the bottom of the third crystallization container. The withdrawn crystal slurry is suction flitered and the mother liquor returned to the crystallization apparatus. The crystals are subsequently washed with water and then with methanol and dried in a vacuum at 40° C. Crude sennosides are obtained with a degree of purity of about 90%. For recovering the butan-2-ol, the butan-2-ol extract is completely evaporated, a dark brown to black residue being obtained. The distillate is again used for the liquid-liquid extraction.

The crude sennosides obtainted are then suspended in an acetone-water mixture (50/50) to give a 10% suspension and completely dissolved by the addition of an aqueous solution of sodium hydroxide until the pH is about 7.5, sodium salt formation thereby taking place. The sennosides are then precipitated out again by adjusting the pH of the solution to 2 with hydrochloric acid. The precipitated product is separated off, briefly washed with aqueous acetone and dried. In this way, there are obtained about 2% (referred to the senna pods used) of pure sennosides (A and B).

What is claimed is:

1. Process for obtaining laxative compounds from senna drug comprising
    (a) extracting the senna drug with aqueous methanol by counter current percolation to obtain an extract;
    (b) concentrating the extract at a temperature not greater than 50° C. until the methanol has been completely removed from the extract to form a concentrate;
    (c) purifying the concentrate obtained by continuous liquid-liquid extraction with an organic solvent to obtain a purified material;
    (d) transferring the purified material to a crystallization apparatus;
    (e) acidifying the purified material, while stirring, to a pH of 1.5 to 2.0 to form an acidified solution;
    (f) seeding the acidified solution with sennoside crystals; and
    (g) separating off the crystalline crude sennoside.

2. Process according to claim 1, wherein 70% methanol is used as extraction solvent in stage (a).

3. Process according to claim 1 or 2, wherein the extraction in stage (a) is carried out at a slightly elevated temperature of at most 35° C.

4. Process according to claim 1, wherein senna pods are swollen in a post-percolate before the percolation step of (a).

5. Process according to claim 1, wherein the concentrate obtained in stage (b) is mixed with about 5% butan-2-ol.

6. Process according to claim 1, wherein the organic solvent used in stage (c) is butanol, methyl ethyl ketone or methyl isopropyl ketone.

7. Process according to claim 6, wherein the organic solvent used is butan-2-ol saturated with water.

8. Process according to claim 7, wherein the run-off ratio of butan-2-ol:raffinate is 0.7 to 0.8:1.

9. Process according to claim 1, wherein acidification in stage (d) is carried out with hydrochloric acid or sulfuric acid.

10. Process according to claim 1, wherein the crude sennosides obtained in stage (d) are, for recrystallization, suspended in an acetone-water mixture to give an approximately 10% suspension, which is completely dissolved by adding sodium hydroxide until the pH is 7.5 to 9, with the formation of sodium salts, whereafter the sennosides are precipitated by adjusting pH of the solution to ca 1.5–2.0, the precipitate separated, washed with water and acetone and dried.

11. The process of claim 1, wherein the crude sennoside is recrystallized.

12. The process of claim 11, wherein the crude sennoside is converted with a pharmacologically compatible base into a pharmacologically compatible salt.

13. A laxative preparation comprising an effective amount of the product of claim 1 and a pharmaceutically acceptable carrier.

* * * * *